(12) United States Patent
Ahn et al.

(10) Patent No.: US 11,771,777 B2
(45) Date of Patent: Oct. 3, 2023

(54) THREE-DIMENSIONAL SELF-ASSEMBLED NUCLEIC ACID NANOPARTICLES AND USE THEREOF

(71) Applicant: KOREA INSTITUTE OF SCIENCE AND TECHNOLOGY, Seoul (KR)

(72) Inventors: Dae-Ro Ahn, Seoul (KR); Thai Bao Dieu Hien, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 363 days.

(21) Appl. No.: 17/085,089

(22) Filed: Oct. 30, 2020

(65) Prior Publication Data
US 2021/0128748 A1    May 6, 2021

(30) Foreign Application Priority Data

Nov. 1, 2019 (KR) ........................ 10-2019-0138846

(51) Int. Cl.
| | |
|---|---|
| *A61K 47/56* | (2017.01) |
| *A61K 47/69* | (2017.01) |
| *A61K 31/7105* | (2006.01) |
| *A61P 13/12* | (2006.01) |
| *C12N 15/113* | (2010.01) |

(52) U.S. Cl.
CPC ...... *A61K 47/6931* (2017.08); *A61K 31/7105* (2013.01); *A61K 47/56* (2017.08); *A61P 13/12* (2018.01); *C12N 15/1135* (2013.01); *C12N 2310/14* (2013.01); *C12N 2310/321* (2013.01); *C12N 2310/351* (2013.01)

(58) Field of Classification Search
None
See application file for complete search history.

(56) References Cited

FOREIGN PATENT DOCUMENTS

KR     1020160012079 A    2/2016

OTHER PUBLICATIONS

Shi et al (ACS Appl Mater Interfaces 8:19353-19363, 2016) (Year: 2016).*
Lee et al (Nat Nanotechno 7:389-393, 2012) (Year: 2012).*
Molitoris, Bruce A., et al., "siRNA Targeted to p53 Attenuates Ischemic and Cisplatin-Induced Acute Kidney Injury", Journal of the American Society of Nephrology 2009, 20 (8), 1754-1764.

* cited by examiner

*Primary Examiner* — Craig D Ricci
(74) *Attorney, Agent, or Firm* — CANTOR COLBURN LLP

(57) ABSTRACT

The present invention relates to three-dimensional self-assembled nucleic acid nanoparticles, a drug delivery system comprising the same, and a pharmaceutical composition for the prevention or treatment of acute kidney injury, which comprises the same. The three-dimensional self-assembled nucleic acid nanoparticles of the present invention, which have a tetrahedral structure, exhibit an excellent renal-targeting ability, and thus the nanoparticles conjugated with the pharmaceutically active ingredient for p53 exhibit excellent p53 and caspase 3 expression reductions in vitro and in vivo, and can thereby be applied to the prevention or treatment of acute kidney injury.

12 Claims, 10 Drawing Sheets
(8 of 10 Drawing Sheet(s) Filed in Color)
Specification includes a Sequence Listing.

[Fig. 6]
| Strand | Sequence | |
|---|---|---|
| siP53-SS | TTCATACACCUAGAAUAUUCACCCUUCA | (SEQ ID NO: 6) |
| siP53-AS | UGAAGGGUGAAAUAUUCUC | (SEQ ID NO: 7) |
| siSC-SS | TTCATACACCACAUGAAGCAGCACGACUU | (SEQ ID NO: 8) |
| siSC-AS | AAGUCGUGCUGCUUCAUGU | (SEQ ID NO: 9) |
[Fig. 7]
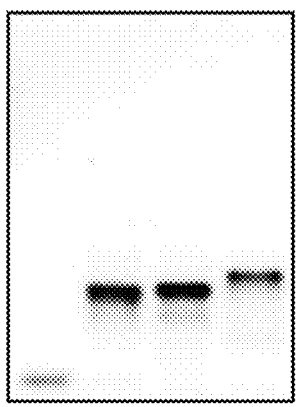
[Fig. 8]
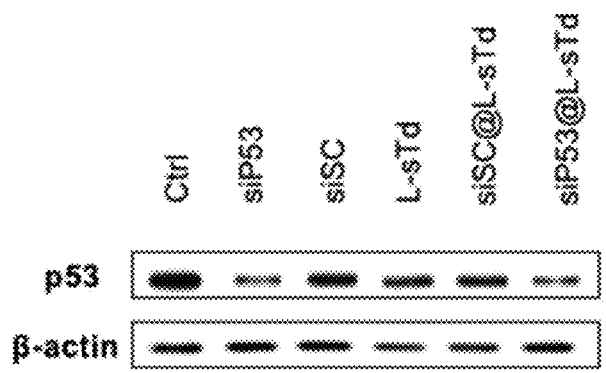

[Fig. 9]
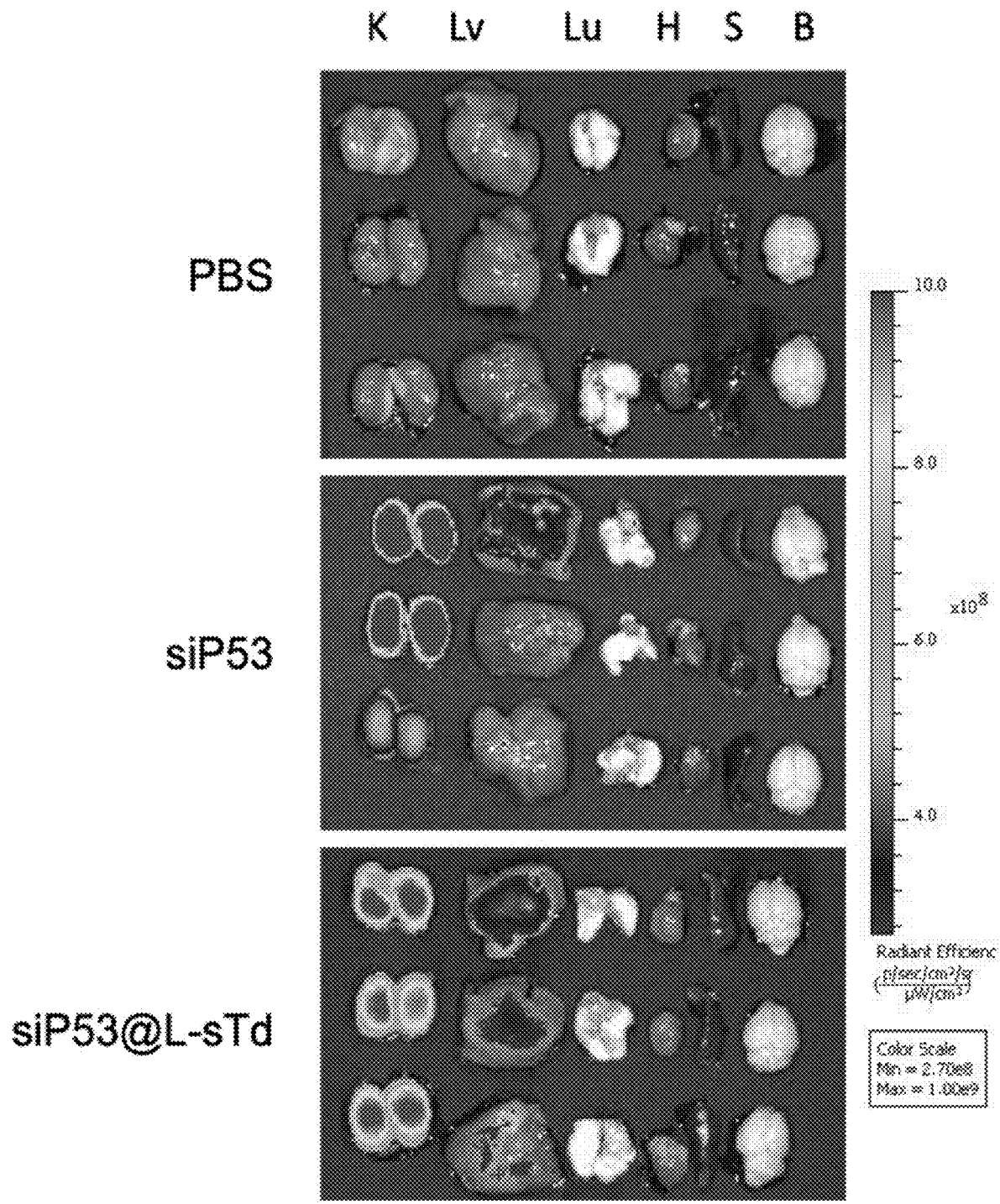

[Fig. 10]
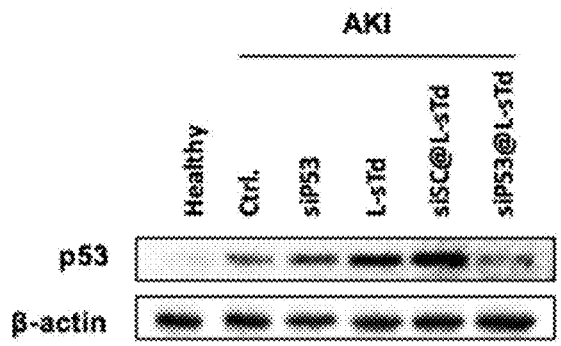
[Fig. 11]
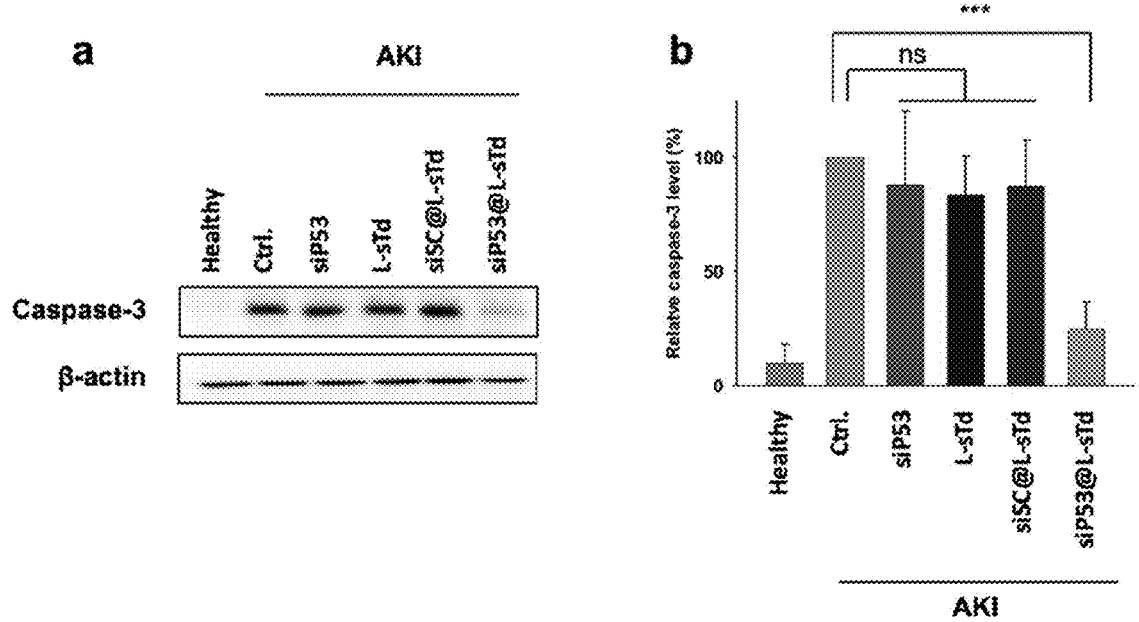

[Fig. 12]
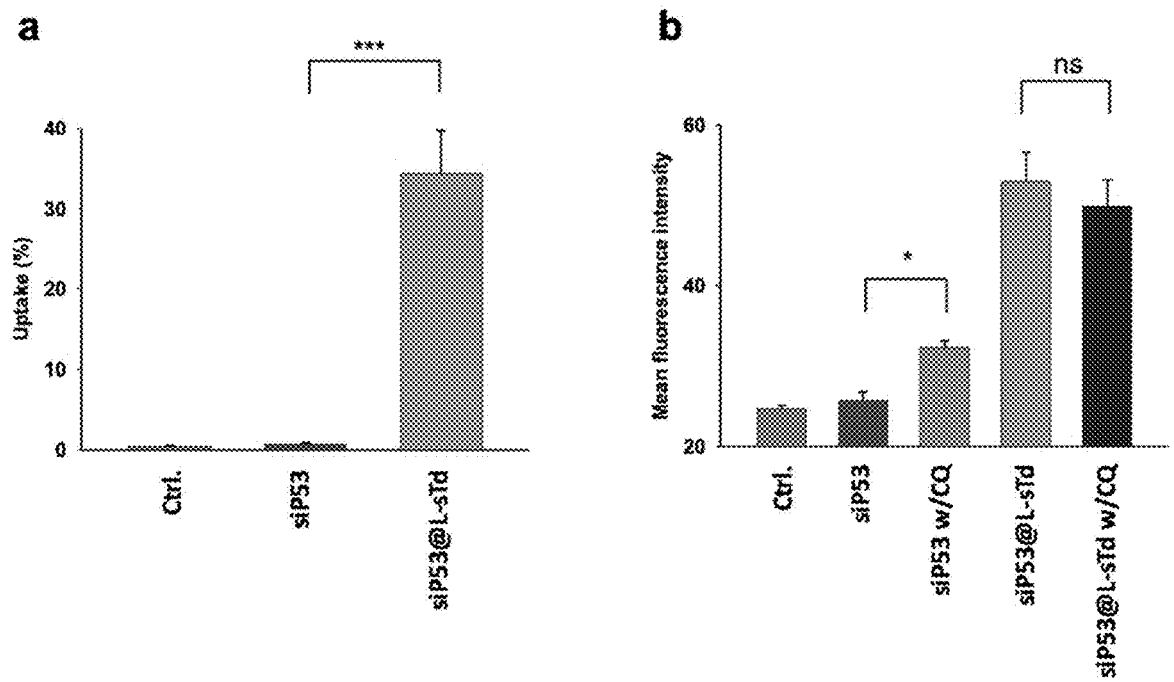

[Fig. 13]
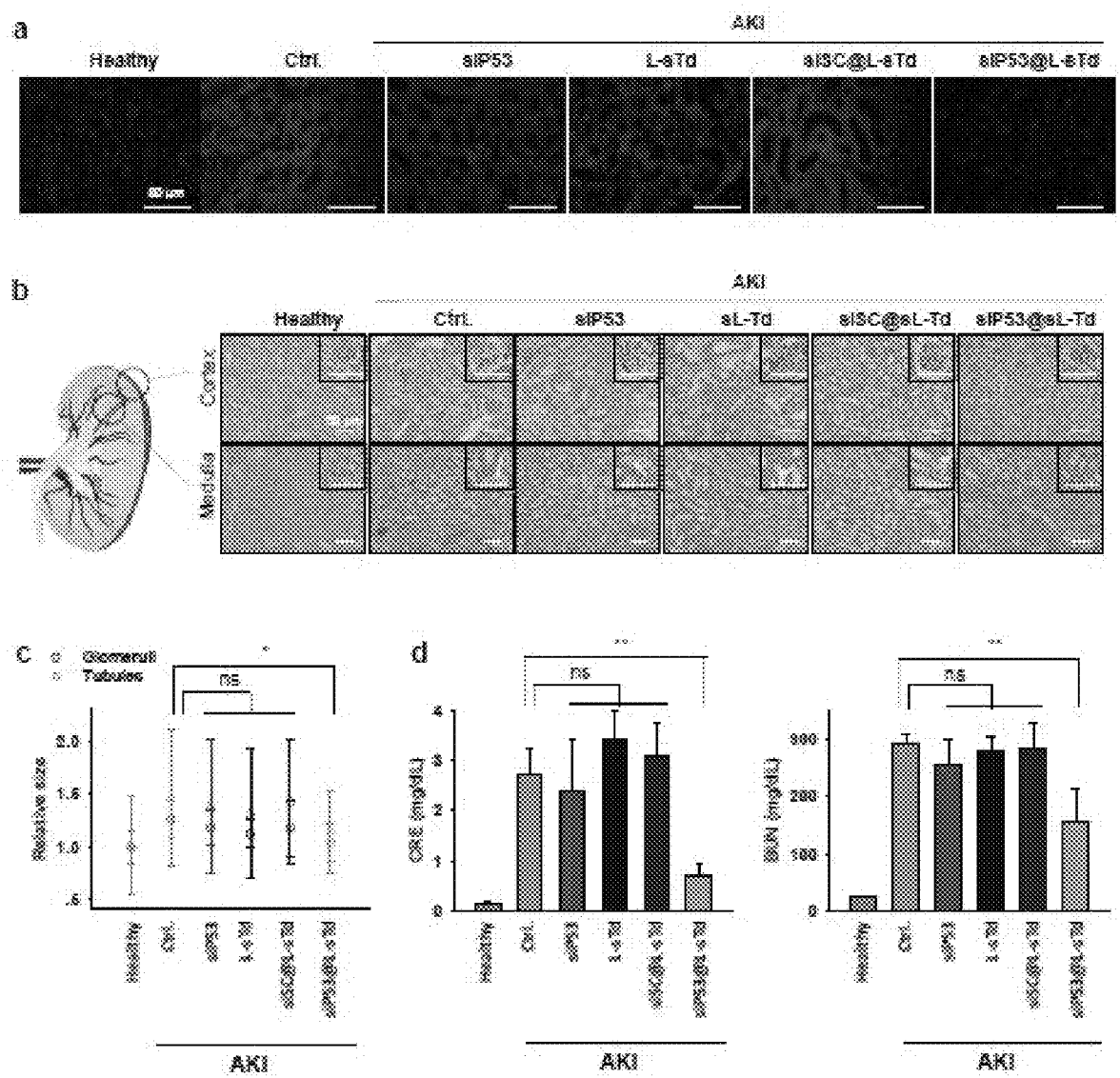

SEQUENCE LISTING

```
<160> NUMBER OF SEQ ID NOS: 13

<210> SEQ ID NO 1
<211> LENGTH: 34
<212> TYPE: DNA
<213> ORGANISM: Artificial Sequence
<220> FEATURE:
<223> OTHER INFORMATION: S1

<400> SEQUENCE: 1
gggatcccga ttcgagacag catttctccc acac                          34
```

```
<210> SEQ ID NO 2
<211> LENGTH: 34
<212> TYPE: DNA
<213> ORGANISM: Artificial Sequence
<220> FEATURE:
<223> OTHER INFORMATION: S2

<400> SEQUENCE: 2
cgtggtaggt tttgctgtct cgttagcgcc ggcc                              34

<210> SEQ ID NO 3
<211> LENGTH: 34
<212> TYPE: DNA
<213> ORGANISM: Artificial Sequence
<220> FEATURE:
<223> OTHER INFORMATION: S3

<400> SEQUENCE: 3
tcgggatccc ttcacgggca acttggccgg cgct                              34

<210> SEQ ID NO 4
<211> LENGTH: 34
<212> TYPE: DNA
<213> ORGANISM: Artificial Sequence
<220> FEATURE:
<223> OTHER INFORMATION: S4

<400> SEQUENCE: 4
acctaccacg ttgttgcccg tgttgtgtgg gaga                              34

<210> SEQ ID NO 5
<211> LENGTH: 44
<212> TYPE: DNA
<213> ORGANISM: Artificial Sequence
<220> FEATURE:
<223> OTHER INFORMATION: S4-linker
<220> FEATURE:
<221> NAME/KEY: misc_feature
<222> LOCATION: (1)..(10)
<223> OTHER INFORMATION: m is 2'-OMe-RNA

<400> SEQUENCE: 5
gguguaugaa acctaccacg ttgttgcccg tgttgtgtgg gaga                   44

<210> SEQ ID NO 6
<211> LENGTH: 29
<212> TYPE: DNA
<213> ORGANISM: Artificial Sequence
<220> FEATURE:
<223> OTHER INFORMATION: siP53-SS

<400> SEQUENCE: 6
ttcatacacc gagaauauuu cacccuuca                                    29

<210> SEQ ID NO 7
<211> LENGTH: 19
<212> TYPE: DNA
<213> ORGANISM: Artificial Sequence
<220> FEATURE:
<223> OTHER INFORMATION: siP53-AS

<400> SEQUENCE: 7
ugaaggguga aauauucuc                                               19

<210> SEQ ID NO 8
```

```
<211> LENGTH: 29
<212> TYPE: DNA
<213> ORGANISM: Artificial Sequence
<220> FEATURE:
<223> OTHER INFORMATION: siSC-SS

<400> SEQUENCE: 8
ttcatacacc acaugaagca gcacgacuu                                          29

<210> SEQ ID NO 9
<211> LENGTH: 19
<212> TYPE: DNA
<213> ORGANISM: Artificial Sequence
<220> FEATURE:
<223> OTHER INFORMATION: siSC-AS

<400> SEQUENCE: 9
aagucgugcu gcuucaugu                                                     19

<210> SEQ ID NO 10
<211> LENGTH: 20
<212> TYPE: DNA
<213> ORGANISM: Artificial Sequence
<220> FEATURE:
<223> OTHER INFORMATION: Mouse p53-F

<400> SEQUENCE: 10
acagcgtggt ggtaccttat                                                    20

<210> SEQ ID NO 11
<211> LENGTH: 18
<212> TYPE: DNA
<213> ORGANISM: Artificial Sequence
<220> FEATURE:
<223> OTHER INFORMATION: Mouse p53-R

<400> SEQUENCE: 11
tatactcaga gccggcct                                                      18

<210> SEQ ID NO 12
<211> LENGTH: 19
<212> TYPE: DNA
<213> ORGANISM: Artificial Sequence
<220> FEATURE:
<223> OTHER INFORMATION: Mouse GADPH-F

<400> SEQUENCE: 12
tgcaccacca actgcttag                                                     19

<210> SEQ ID NO 13
<211> LENGTH: 19
<212> TYPE: DNA
<213> ORGANISM: Artificial Sequence
<220> FEATURE:
<223> OTHER INFORMATION: Mouse GADPH-R

<400> SEQUENCE: 13
ggatgcaggg atgatgttc                                                     19
```

THREE-DIMENSIONAL SELF-ASSEMBLED NUCLEIC ACID NANOPARTICLES AND USE THEREOF

CROSS-REFERENCE TO RELATED APPLICATION

This application claims the benefit of Korean Patent Application No. 10-2019-0138846, filed on Nov. 1, 2019, in the Korean Intellectual Property Office, the disclosure of which is incorporated herein in its entirety by reference.

SEQUENCE LISTING

A Sequence Listing, incorporated herein by reference, is submitted in electronic form as an ASCII text file, created Oct. 29, 2020, having size 4.0 Kb, and named "8N33511.txt".

TECHNICAL FIELD

The present invention relates to three-dimensional self-assembled nucleic acid nanoparticles, a drug delivery system comprising the same, and a pharmaceutical composition for the prevention or treatment of acute kidney injury, which comprises the same.

BACKGROUND ART

The kidneys play a very central role in regulating homeostasis and maintaining the body's electrolyte balance. When the kidneys are damaged or function improperly, toxic waste and non-essential liquids may be accumulated in the body and may cause life-threatening syndromes. Acute kidney injury (AKI) is a potentially fatal disease characterized by the decrease in urine volume and the maintenance of harmful nitrogen metabolism for a period of 7 days or less, leading to acute and reversible decline in kidney function. AKI is typically found in hospitalized patients (7% to 20%) or in patients admitted to the intensive care unit (50%). The major causes of AKI are ischemia/reperfusion, sepsis, and accumulation of nephrotoxic substances/drugs. In addition, patients suffering from AKI are at increased risk of developing a chronic kidney disease (CDK), followed by an end-stage renal disease (ESRD), resulting in high mortality. Currently, as a therapy for AKI, universal treatments such as blood pressure management, administration at the early stages of AKI, and introduction of dialysis or renal replacement therapy are conventionally used. As the understanding of structural and functional kidney disease at the molecular and microvascular levels gradually improves, treatments which target specific enzymes and molecules in cascade pathways related to microvascular disorders, immunomodulatory disorders, and oxidative stress through molecules that inhibit AKI derived from ongoing pathways have been found to have some therapeutic efficacy against AKI in a rat model, but have not yet been confirmed in humans.

Advanced therapies such as gene therapy are promising techniques for AKI therapy because they provide a more direct and targeted approach to arresting the expression of AKI-related proteins by triggering the RNAi pathway using siRNA. Due to the renal preference property, siRNA is rapidly absorbed into the kidneys and reabsorbed into the renal proximal tubule, thereby prolonging the siRNA retention time at the target site to effectively inhibit the target protein. The RNAi strategy against AKI can be achieved by targeting appropriate genes that play an important role in disease progression.

Meanwhile, p53 is a stress-responsive gene activated by DNA damage, hypoxia, oxidative stress, and other conditions, and induces cell cycle arrest, cell senescence, and apoptosis (programmed cell death). In the acute phase, when p53 is temporarily inhibited at the time of injury, programmed cell death can be alleviated and cell damage repaired, thereby preserving the integrity and function of tissues and organs. Preclinical studies have confirmed that p53-targeted siRNA can protect the kidneys from ischemia reperfusion (IR)-induced AKI in various clinically relevant animal models.

The siRNA-based therapy has tremendous potential, but the benefits of this therapy for AKI patients remain elusive as siRNA raises concerns about instability, immune tolerance, and off-target effects. To solve this problem, it is desirable to plan local delivery of siRNA to the kidney-targeting site.

Under this background, the present inventors prepared tetrahedral nanoparticles of highly kidney-targeted L-DNA, and completed the present invention by confirming that the tetrahedral nanoparticles conjugated with p53 siRNA, which is a pharmaceutical active ingredient for p53, exhibit a renoprotection effect in AKI-infected subjects.

DISCLOSURE

Technical Problem

An object of the present invention is to provide a kidney-specific drug delivery system comprising three-dimensional self-assembled nucleic acid nanoparticles having a tetrahedral structure.

Another object of the present invention is to provide a pharmaceutical composition for preventing or treating acute kidney injury, comprising: a kidney-specific drug delivery system comprising three-dimensional self-assembled nucleic acid nanoparticles having a tetrahedral structure; and at least one of siRNA, shRNA, an antisense oligonucleotide, or microRNA bound to the drug delivery system.

Still another object of the present invention is to provide a method for preventing or treating acute kidney injury, comprising a step of administering to a subject a pharmaceutical composition for preventing or treating acute kidney injury comprising: a kidney-specific drug delivery system comprising three-dimensional self-assembled nucleic acid nanoparticles having a tetrahedral structure; and at least one of siRNA, shRNA, an antisense oligonucleotide, or microRNA bound to the drug delivery system.

Technical Solution

The present invention will be described in detail as follows. Meanwhile, each description and embodiment disclosed in the present invention can also be applied to each of the other descriptions and embodiments. That is, all combinations of various elements disclosed in the present invention belong to the scope of the present invention. In addition, the scope of the present invention cannot be considered as being limited by the specific description provided below.

An aspect of the present invention for achieving the objects described above provides a kidney-specific drug delivery system comprising three-dimensional self-assembled nucleic acid nanoparticles having a tetrahedral structure.

In the present invention, the term "acute kidney injury (AKI)" refers to a disease characterized by the decrease in urine volume and the maintenance of harmful nitrogen metabolism for a period of 7 days or less, which is caused by ischemia/reperfusion, sepsis, and accumulation of nephrotoxic substances/drugs, leading to acute and reversible decline in kidney function. Patients suffering from AKI are at increased risk of developing a chronic kidney disease (CDK), followed by an end-stage renal disease (ESRD), resulting in high mortality.

In the present invention, the term "nanoparticle" broadly refers to a particle having a diameter of several to several hundreds of nanometers. The method of preparation is largely divided into three methods: a top-down approach, which is a physical method; a bottom-up approach based on a chemical synthesis method; and a self-assembly method. The last method (self-assembly) is currently the basis for the assembly of biomolecular nanotechnologies, which is a kind of bottom-up approach. The components of the particles spontaneously aggregate to form nanoparticles due to their physical, chemical, and structural properties. In particular, the size of the particles may be determined by adjusting the molar ratio of the reactant. In addition, the formed nanoparticles may be applied to various fields by modifying the surface to improve their physical properties.

For the purposes of the present invention, the nanoparticles may be nucleic acid nanoparticles consisting of nucleic acids, but are not limited thereto.

The nucleic acid nanoparticles may include one or more oligonucleotides selected from the group consisting of SEQ ID NOs: 1 to 8, but do not exclude addition of a meaningless sequence upstream or downstream of the nucleotide sequences of SEQ ID NOs: 1 to 8, a mutation that may occur naturally, or a silent mutation thereof, and it is apparent to those skilled in the art that any of these will correspond to the oligonucleotide of the present invention as long as it has an activity which is the same as or corresponding to that of the oligonucleotide including the nucleotide sequences of SEQ ID NOs: 1 to 8. As a specific example, the oligonucleotide of the present invention may consist of the nucleotide sequences of SEQ ID NOs: 1 to 8 or a nucleotide sequence having a homology or identity of at least 80%, 85%, 90%, 95%, 96%, 97%, 98%, or 99% or more to the nucleotide sequences of SEQ ID NOs: 1 to 8. In addition, it is apparent that an oligonucleotide consisting of a nucleotide sequence, in which part of the sequence is deleted, modified, substituted, or added, is included within the scope of the oligonucleotide of the present invention, as long as the oligonucleotide has the above homology or identity and exhibits an effect corresponding to the oligonucleotide according to the present invention.

That is, in the present invention, even when it is described as an "oligonucleotide consisting of a nucleotide sequence represented by a specific SEQ ID NO", it is apparent that as long as it has an activity which is the same as or corresponding to that of the oligonucleotide consisting of the nucleotide sequence of the corresponding SEQ ID NO, the oligonucleotide consisting of a nucleotide sequence, in which part of the sequence is deleted, modified, substituted, or added, can also be used in the present invention. For example, it is apparent that an "oligonucleotide consisting of a nucleotide sequence of SEQ ID NO: 1" can belong to the "oligonucleotide consisting of a nucleotide sequence of SEQ ID NO: 1" of the present invention as long as long as it has an activity identical or corresponding thereto.

In the present invention, the term "oligonucleotide" refers to a synthesized short-stranded DNA or RNA molecule.

The oligonucleotide may be single-stranded, but is not limited thereto.

The oligonucleotide may include a chemical or physical modification of one or more of nucleotides constituting the oligonucleotides. The chemical or physical modification may include, for example, any one or more modifications selected from the group consisting of substitution with an optical isomer, a sugar-modified nucleotide, a base-modified nucleotide, a phosphorothioate nucleic acid, a phosphorodithioate nucleic acid, a phosphoroamidate nucleic acid, an amide-linked nucleic acid, an MMI-linked nucleic acid, an alpha-nucleic acid, and a methylphosphonate nucleic acid, but is not limited thereto, and may include any modifications known in the art without limitation.

The substitution with an optical isomer may include, for example, substitution with at least one of D-DNA and L-DNA, but is not limited thereto.

The sugar-modified nucleotide may be, for example, 2'-fluoro-RNA, 2'-O-methoxy-RNA, 2'-amino RNA, a 2'-O-alkyl nucleic acid, a 2'-O-allyl nucleic acid, a 2'-O-alkynyl nucleic acid, a hexose nucleic acid, pyranosyl RNA, and an anhydrohexitol nucleic acid, and specifically may be at least one of 2'-fluoro-RNA and 2'-O-methoxy-RNA, but the sugar-modified nucleotide is not limited thereto.

For the purposes of the present invention, the entirety of the nucleotides forming the oligonucleotide may consist of any one selected from the group consisting of D-DNA, L-DNA, 2'-fluoro-RNA, and 2'-O-methoxy-RNA, but the nucleotides are not limited thereto.

The nucleic acid nanoparticle may be formed by self-assembly of a plurality of single-stranded nucleic acids, such as 4 to 100, 4 to 50, or 4 to 20 strands of nucleic acids according to a hybridization principle, and specifically, the number of oligonucleotides forming the nucleic acid nanoparticle may be four, but these are not limited thereto.

The four oligonucleotides forming the nucleic acid nanoparticle may include four kinds of oligonucleotides selected from the group consisting of the nucleotide sequences of SEQ ID NOs: 1 to 8, and specifically, the four kinds of oligonucleotides may include oligonucleotides consisting of the nucleotide sequences of SEQ ID NOs: 1 to 4, but the oligonucleotides are not limited thereto.

The oligonucleotides consisting of the nucleotide sequence of SEQ ID NOs: 1 to 4 may include the chemical or physical modifications described above, and specifically may consist of any one of 2'-fluoro-RNA and 2'-O-methoxy-RNA, but are not limited thereto.

For the purposes of the present invention, the entirety of the base sequences forming the oligonucleotides of SEQ ID NOs: 1 to 4 may consist of any one of 2'-fluoro-RNA and 2'-O-methoxy-RNA, but are not limited thereto.

The nucleic acid nanoparticle may include a double-stranded nucleic acid including a hybridization region in which the oligonucleotide and the oligonucleotide hybridizing thereto are hybridized, and the double-stranded nucleic acid may form a side of a surface of a nucleic acid nanoparticle structure, but these are not limited thereto.

Although the overall shape and the size of sTds (D-DNA (D-sTd), L-DNA (L-sTd), 2'-O-Me-RNA (M-sTd), and 2'-FRNA (F-sTd)) are very similar to one another, the kidney accumulation level of sTds is surprisingly different depending on the backbone type. Only the Td with L-DNA backbone (L-sTd) shows substantially kidney-preferred distribution upon intravenous injection. While the serum-degradable backbone of D-DNA could be an obvious factor for the in vivo behavior of D-sTd as distinguished from that of L-sTd, the lack of kidney-preference in M-sTd and F-sTd, which are based on backbones with similar serum stability to L-sTd, could be due to differences in the chemical nature of their backbones from that of L-DNA.

Despite D-DNA backbone-based structures, the densely packed structural aspect of DNA origami nanostructures (DONs) greatly improves serum stability, which contributes to their kidney-preferential distribution. The shape-dependent kidney accumulation property is observed in DONs even though their sizes (90 nm to 400 nm) are much larger than that of L-sTd. This indicates that the kidney-targeting property of nucleic acid nanostructures is not driven by just one factor, but can be obtained by fine-tuning of various factors including size, shape, and backbone type.

According to the characteristics described above, the three-dimensional self-assembled nucleic acid nanoparticles of the present invention have tissue specificity for the kidneys even without targeting ligands when administered in vivo. Therefore, the drug delivery system, which includes the three-dimensional self-assembled nucleic acid nanoparticles, is characterized in that it delivers a pharmaceutically active ingredient specifically to the kidneys.

The drug delivery system may further include a pharmaceutically active ingredient.

The pharmaceutical active ingredient may be specifically delivered to the organ (kidney) by the drug delivery system, and specifically may be bound to the nucleic acid backbone of the three-dimensional self-assembled nucleic acid nanoparticles or collected inside the nucleic acid nanoparticles for the delivery, but the pharmaceutical active ingredient is not limited thereto.

The pharmaceutical active ingredient may be at least one of a drug and a nucleic acid, and may be used for preventing or treating diseases. For example, the drug may be contrast agents, hormones, anti-hormones, vitamins, calcium agents, mineral preparations, saccharides, organic acid preparations, protein amino acid preparations, antidote, enzyme preparations, metabolic preparations, tissue revitalization drugs, chlorophyll preparations, coloring preparations, radiopharmaceuticals, tissue cell diagnostic agents, tissue cell therapy agents, antibiotic agents, antiviral agents, complex antibiotic agents, chemotherapy agents, vaccines, toxins, toxoids, antitoxin, leptospira serum, blood products, biological agents, analgesics, immunogenic molecules, antihistamines, allergy medicines, non-specific immunogen agents, anesthetics, stimulants, psychotropic solvent, a peptide, and the like, but is not limited thereto. In addition, the nucleic acid may be an aptamer, an antisense oligonucleotide, micro RNA, siRNA, and shRNA, but the nucleic acid is not limited thereto.

Another aspect of the present invention provides a pharmaceutical composition for preventing or treating acute kidney injury, comprising: a kidney-specific drug delivery system comprising three-dimensional self-assembled nucleic acid nanoparticles having a tetrahedral structure; and a pharmaceutically active ingredient bound to the drug delivery system.

The terms as used herein are as described above.

The pharmaceutical composition may include an oligonucleotide including D-DNA or L-DNA bound to the 3' end of any one of four oligonucleotides forming a three-dimensional self-assembled nucleic acid nanoparticle of the drug delivery system; an oligonucleotide hybridized to the oligonucleotide to form a double bond; and a pharmaceutically active ingredient bound to the oligonucleotide forming the double bond; that is, the pharmaceutical composition may be one in which the pharmaceutically active ingredient is bound to the nucleic acid backbone of a three-dimensional self-assembled nucleic acid nanoparticle, but is not limited thereto.

The pharmaceutically active ingredient bound to the nucleic acid backbone of the three-dimensional self-assembled nucleic acid nanoparticle may be bound in the form of an overhang arm to an end where 10-mer nucleotides are further extended from the vertex of the three-dimensional self-assembled nucleic acid nanoparticle, but is not limited thereto.

The pharmaceutical active ingredient inhibits a gene that upregulates an apoptosis pathway. For example, the gene which upregulates an apoptosis pathway may be any one or more selected from the group consisting of p53, Fas, a tumor necrosis factor-related apoptosis-inducing ligand (TRAIL), a tumor necrosis factor (TNF), receptors thereof, bcl-2, and caspase, and specifically may be p53, but is not limited thereto.

The pharmaceutically active ingredient may be a nucleic acid, and specifically may be any one or more selected from the group consisting of siRNA, shRNA, an antisense oligonucleotide, and microRNA, and more specifically may be siRNA, but the pharmaceutically active ingredient is not limited thereto. In one embodiment of the present invention, the siRNA for p53 may include nucleotide sequences of SEQ ID NO: 9 and SEQ ID NO: 10, but is not limited thereto, and any siRNA known in the art may be used without limitation.

The pharmaceutical composition of the present invention has a use in the "prevention" and/or "treatment" of acute kidney injury. For the pharmaceutical composition for its use in the prevention, it is administered to a subject who has or is suspected of being at risk of developing the disease, disorder, or condition described herein. That is, it can be administered to a subject at risk of developing acute kidney injury. For the pharmaceutical composition for its use in the treatment, it is administered to a subject, such as a patient already suffering from the disorder described herein, in an amount sufficient to treat or at least partially arrest the symptoms of the disease, disorder, or condition described herein. The amount effective for this use may vary depending on the severity and course of the disease, disorder, or condition, prior treatment, the individual's health status and responsiveness to the drug, and the determination of the physician or veterinarian.

It may further include a suitable carrier, excipient, or diluent commonly used in the preparation of the pharmaceutical composition of the present invention. The content of the active ingredient included in the composition is not particularly limited, but may be included at 0.0001 wt % to 10 wt %, preferably 0.001 wt % to 1 wt % based on the total weight of the composition.

The pharmaceutical composition may have any one formulation selected from the group consisting of tablets, pills, powders, granules, capsules, suspensions, liquid preparations for internal use, emulsions, syrups, sterilized aqueous solutions, non-aqueous solvents, freeze-dried agents, and suppositories, and may be of various oral or parenteral formulations. For formulation, the composition is prepared using commonly used diluents or excipients such as fillers, extenders, binders, wetting agents, disintegrants, and surfactants. Examples of the solid formulation for oral administration include tablets, pills, powders, granules, capsules, and the like, and these solid formulations are prepared by mixing one or more compounds with at least one excipient or more, such as starch, calcium carbonate, sucrose, lactose, gelatin, and the like. Additionally, in addition to simple excipients, lubricants such as magnesium stearate, talc, and the like are also used. Examples of the liquid formulation for oral administration include suspensions, liquid preparations for internal use, emulsions, syrups, and the like, and may include various excipients such as wetting agents, sweetening agents, fragrances, and preservatives in addition to water and liquid paraffin, which are commonly used simple diluents. Examples of the formulation for parenteral administration include sterilized aqueous solutions, non-aqueous solutions, suspensions, emulsions, lyophilized formulations, and suppositories. For the non-aqueous solvent and suspension, propylene glycol, polyethylene glycol, vegetable oil such as olive oil, injectable ester such as ethyl oleate, and the like may be used. As a base for suppositories, witepsol, macrogol, tween 61, cacao butter, laurin butter, glycerogelatin, and the like may be used.

The composition of the present invention can be administered to a subject in a pharmaceutically effective amount.

In the present invention, the term "pharmaceutically effective amount" means an amount sufficient to treat a disease at a reasonable benefit/risk ratio applicable to medical treatment, and the level of effective dosage can be determined according to the type, severity, age, sex of the individual, type of disease, activity of the drug, sensitivity to the drug, time of administration, route of administration and rate of excretion, the duration of treatment, factors including the drugs used simultaneously, and other factors well known in the medical field. The composition of the present invention can be administered as an individual therapeutic agent or administered in combination with other therapeutic agents, and can be administered sequentially or simultaneously with a conventional therapeutic agent. In addition, the composition of the present invention can be administered alone or in combination. It is important to administer the pharmaceutical composition in the minimum amount that can exhibit the maximum effect without causing side effects, in consideration of all of the factors described above, which may be easily determined by those skilled in the art. The preferred dosage of the composition of the present invention may vary according to the condition and weight of the patient, the degree of the disease, the form of the drug, and the route and duration of administration, and the administration may be conducted once a day, or may also be conducted several times a day. The composition of the present invention can be administered to any subject that requires the prevention or treatment of acute kidney injury, without particular limitation. The composition of the present invention can be administered by various conventional methods. For example, the composition of the present invention can be administered by oral or rectal administration, or by intravenous, intramuscular, subcutaneous, intrauterine dural, or cerebrovascular injection.

The pharmaceutical composition of the present invention can be administered to a subject who has developed and progressed or has a high likelihood of developing acute kidney injury, thereby preventing the occurrence of acute kidney injury or alleviating the degree of occurrence.

Still another aspect of the present invention provides a method for preventing or treating acute kidney injury, comprising a step of administering to a subject a pharmaceutical composition for preventing or treating acute kidney injury comprising: a kidney-specific drug delivery system comprising three-dimensional self-assembled nucleic acid nanoparticles having a tetrahedral structure; and a pharmaceutically active ingredient bound to the drug delivery system.

The terms as used herein are as described above.

The pharmaceutical active ingredient inhibits a gene that upregulates an apoptosis pathway, but is not limited thereto. Specifically, the gene upregulating an apoptosis pathway may be any one or more selected from the group consisting of p53, Fas, a tumor necrosis factor-related apoptosis-inducing ligand (TRAIL), a tumor necrosis factor (TNF), receptors thereof, bcl-2, and caspase, and more specifically, the gene may be p53.

The pharmaceutical active ingredient may be any one or more selected from the group consisting of siRNA, shRNA, an antisense oligonucleotide, and microRNA, and more specifically siRNA, but is not limited thereto.

In the present invention, the term "subject" refers to all animals that have developed or may develop acute kidney injury, and the pharmaceutical composition of the present invention can efficiently treat a subject by administering the pharmaceutical composition to the subject suspected of having acute kidney injury.

In the present invention, the term "administration" means introducing the pharmaceutical composition of the present invention to a subject suspected of having acute kidney injury by any suitable method, and as long as the route of administration can reach the target tissue, the composition of the present invention can be administered through various routes, either an oral or parenteral route.

The pharmaceutical composition of the present invention can be administered in a pharmaceutically effective amount.

In the present invention, the term "pharmaceutically effective amount" means an amount sufficient to treat a disease at a reasonable benefit/risk ratio applicable to medical treatment, and the level of effective dosage can be determined according to the type, severity, age, sex of the individual, type of disease, activity of the drug, sensitivity to the drug, time of administration, route of administration and rate of excretion, the duration of treatment, factors including the drugs used simultaneously, and other factors well known in the medical field. The composition of the present invention can be administered as an individual therapeutic agent or administered in combination with other therapeutic agents, and can be administered sequentially or simultaneously with a conventional therapeutic agent. In addition, the composition of the present invention can be administered alone or in combination. It is important to administer the pharmaceutical composition in the minimum amount that can exhibit the maximum effect without causing side effects, in consideration of all of the factors described above, which may be easily determined by those skilled in the art.

The pharmaceutical composition of the present invention can be administered to any subject that requires the prevention or treatment of acute kidney injury, without particular limitation. For example, the composition of the present invention can be applied to any of non-human animals such as monkey, dog, cat, rabbit, guinea pig, rat, mice, cow, sheep, pig, goat, bird and fish, and so on, and the pharmaceutical composition can be administered parenterally, subcutaneously, intraperitoneally, and intranasally. For topical treatment, if necessary, it can be administered by a suitable method including intralesional administration. The preferred dosage of the pharmaceutical composition of the present invention varies according to the condition and weight of the individual, the severity of the disease, the form of the drug, the route and duration of administration, but may be appropriately selected by those skilled in the art. For example, the composition of the present invention can be administered by oral or rectal administration, or by intravenous, intramuscular, subcutaneous, intrauterine dural, or cerebrovascular injection, but is not limited thereto.

An appropriate total amount of administration per 1 day of the pharmaceutical composition of the present invention can be determined by a physician within the range of correct medical determination, and is generally 0.001 mg/kg to 1,000 mg/kg, preferably 0.05 mg/kg to 200 mg/kg, more preferably 0.1 mg/kg to 100 mg/kg once a day, or can be administered in divided doses multiple times daily.

Advantageous Effects

The three-dimensional self-assembled nucleic acid nanoparticles having a tetrahedral structure according to the present invention and a drug delivery system comprising the same exhibit an excellent renal-targeting ability, and thus the nanoparticles conjugated with the pharmaceutically active ingredient for p53 exhibit excellent p53 and caspase-3 expression reductions in vitro and in vivo, and thus can be applied to the prevention or treatment of acute kidney injury.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6. Sense (SS) and antisense (AS) sequences of siRNA used. RNA is indicated with blue, and 2'-O-Me-RNA is indicated with red. The DNA sequences complementary to the linker are underlined.

FIG. 7. L-sTd loaded with siP53 (siP53@L-sTd) was characterized by agarose gel electrophoresis. Mobility of siP53@L-sTd was slightly reduced compared with that of L-sTd and L-sTd with the linker overhang.

FIG. 8. Representative image of western blotting of p53 in TCMK-1 cells. The β-actin level was used as the internal control to determine the relative p53 level.

FIG. 9. Ex vivo imaging of major organs from AKI mice treated with PBS, siP53, and siP53@L-sTd (K, kidney; Lv, liver; Lu, lung; H, heart; S, spleen; B, brain).

FIG. 10. Representative image of western blotting of p53 in kidney lysate. The β-actin level was used as the internal control to determine the relative p53 level.

FIG. 11. (a) Representative image of western blotting of caspase-3 in kidney lysate. (b) Relative caspase-3 levels in kidney lysate estimated by western blotting (mean±SD; n=5; ***$P<0.001$; ns, non-significant). The β-actin level was used as the internal control to determine the relative caspase-3 level.

FIG. 12. (a) Cellular uptake efficiency of siP53 and siP53@L-sTd in TCMK-1 cells. (b) Mean fluorescence intensity of TCMK-1 cells treated with siP53 and siP53@L-sTd in the presence or in the absence of chloroquine (CQ) (mean±SD; n=3; *$P<0.05$; ***$P<0.001$; ns, non-significant).

FIG. 13. Alleviation of AKI damage by siP53 delivered by L-sTd. (a) Images of kidney sections stained with Cy5-labeled annexin V (red). Nuclei were stained with DAPI (blue). Scale bars indicate 80 µm. (b) Images of cortex and medullar regions in kidney sections stained with H&E. Representative glomeruli and tubules are displayed in insets. Red arrows indicate widened Bowman's space in glomeruli. White arrows indicate enlarged tubules. Scale bars indicate 50 µm. (c) Relative sizes of glomeruli and tubules estimated in the section images (mean±SD; n=16 for glomeruli; n=49 for tubules; *$P<0.05$; ns, non-significant). (d) Creatine (CRE) and blood urea nitrogen (BUN) levels estimated in blood samples of mice (mean±SD; n=4; **$P<0.01$; ns, non-significant).

DETAILED DESCRIPTION

Hereinafter, the present invention will be described in more detail by way of examples. However, it will be apparent to those of ordinary skill in the art to which the present invention pertains that these examples are for illustrative purposes of the present invention, and the scope of the present invention is not limited by these examples.

Example 1. Oligonucleotide Synthesis

Figure 1:
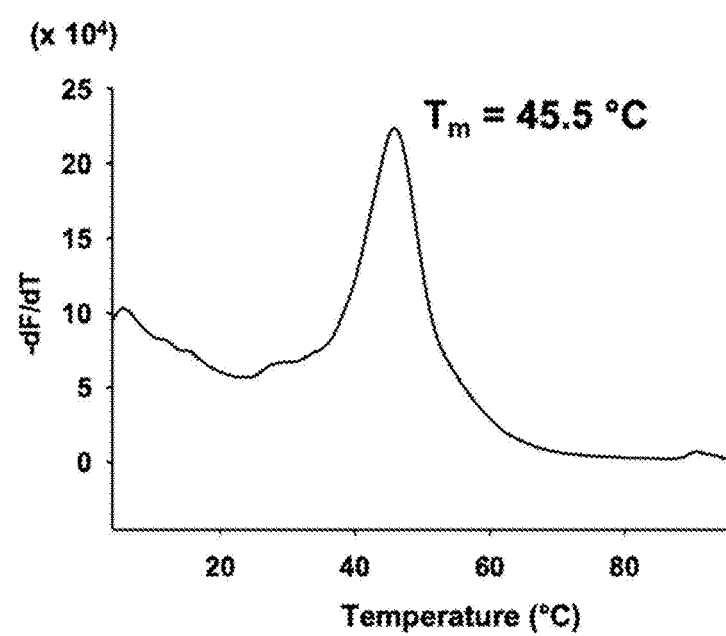
FIG. 1. Melting temperature of D-sTd (300 nM) in TM buffer.

For effective accumulation in the kidney, a DNA tetrahedron with smaller size and higher cellular uptake efficiency is desired. However, the duplex side of the DNA tetrahedron should also have sufficient number of base pairs (bp) for stable assembly of the nanostructure at the physiological temperature (37° C.) while keeping the size of the DNA tetrahedron small enough to be filtered through GBM. Therefore, the tetrahedron was designed with 10 bp per side as the core structure to develop kidney-targeted siRNA carriers, with a sufficiently small size and melting temperature much higher than 37° C. (FIG. 1).

Figure 2:
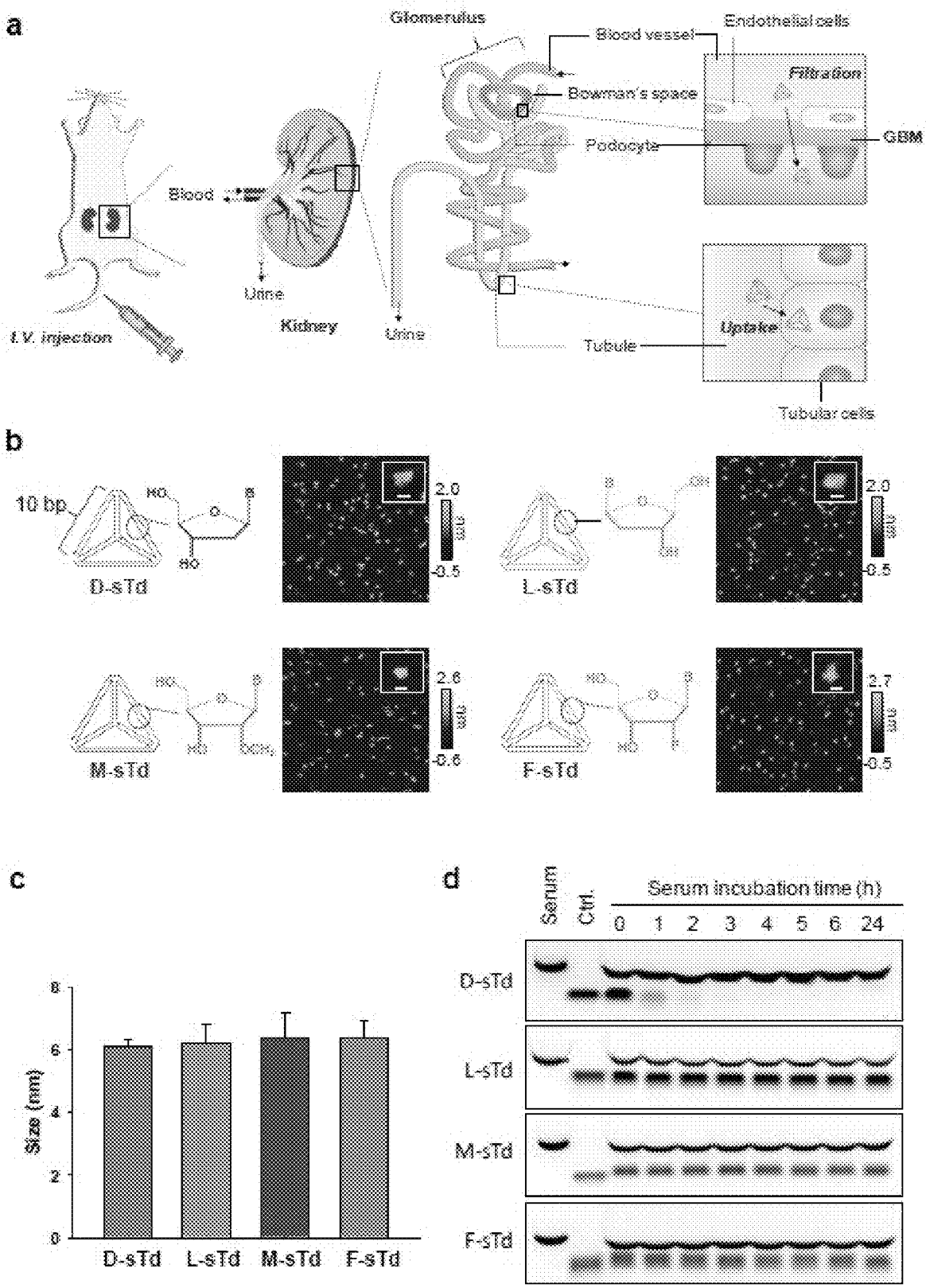
FIG. 2. Systemic kidney delivery of sTds. (a) Intravenously injected small tetrahedrons (sTds) are filtered through GBM and Bowman's space to enter tubules where the nanoconstructs taken up into tubular cells. (b) AFM images of sTds with their schematic structures. The insets display representative images of sTds. Scale bars indicate 10 nm. (c) Hydrodynamic sizes of sTds (1 µM) in TM buffer measured by dynamic light scattering. (d) sTds were incubated in 50% mouse serum solution and analyzed by agarose gel (1%) electrophoresis. The control (ctrl.) indicates sTds in the absence of serum.

Specifically, four small tetrahedrons (sTds) with 10 bp per side were prepared with different sugar backbones such as D-DNA (D-sTd), L-DNA (L-sTd), 2'-O-Me-RNA (M-sTd), and 2'-FRNA (F-sTd) (Table 1 and FIG. 2b).

Sequences of the oligonucleotides used to construct sTds in Table 1. *U was used instead of T for M-sTd and F-sTd. The 2'-O-Me-RNA linker used for siP53@L-sTd is indicated with underline.

TABLE 1

| Strand | Sequence |
| --- | --- |
| S1 | GGGATCCCGATTCGAGACAGCATTTCTCCCACAC (SEQ ID NO: 1) |
| S2 | CGTGGTAGGTTTTGCTGTCTCGTTAGCGCCGGCC (SEQ ID NO: 2) |
| S3 | TCGGGATCCCTTCACGGGCAACTTGGCCGGCGCT (SEQ ID NO: 3) |
| S4 | ACCTACCACGTTGTTGCCCGTGTTGTGTGGGAGA (SEQ ID NO: 4) |
| S4-linker | GGUGUAUGAAACCTAC-CACGTTGTTGCCCGTGTTGTGTGGGAGA (SEQ ID NO: 5) |

Oligonucleotides used for assembly of sTds were synthesized on a Mermaid 4 DNA synthesizer (Bioautomation, USA) using controlled-pore glass (CPG) resin (Glen Research, USA) at a 1 mol scale. The oligonucleotides were cleaved from CPG and de-protected in concentrated $NH_3$ (30%) at 55° C. for 16 h. Crude oligonucleotides were purified by denaturing polyacrylamide gel electrophoresis (dPAGE). The oligonucleotides in the excised gel were crushed and incubated in 0.2×TBE (30 mL) with gentle shaking overnight. The supernatant containing extracted oligonucleotides was mixed with n-butanol thoroughly and centrifuged (3000 rpm, 3 min). The upper phase (n-butanol phase) was decanted. This extraction step was performed repeatedly until the aqueous phase volume was decreased to approximately 500 μL. To the aqueous phase (500 μL) were added 3 M sodium acetate (pH 5.2, 50 μL) and 2.5 volumes of pure ethanol, and this was then stored at −80° C. for 2 h. The precipitated pellet was collected after 20 min centrifugation at 13,000 rpm. Finally, the pellet was washed with 70% ethanol (200 μL), dried, and re-suspended in distilled water. All purified oligonucleotides were quantified by a Genesys 10S UV/Vis Spectrophotometer (ThermoFisher Scientific, USA).

The oligonucleotides were characterized by electrospray ionization mass spectrometry (ESI-MS) (Tables 1 and 2).

TABLE 2

| Sequence | | Calculated [M − H]⁻ | Observed [M − H]⁻ |
| --- | --- | --- | --- |
| D-sTd | S1 | 10946.3 | 10949.3 |
| | S2 | 10642.8 | 10643.5 |

TABLE 2-continued

| Sequence | | Calculated [M − H]⁻ | Observed [M − H]⁻ |
| --- | --- | --- | --- |
| | S3 | 10590.7 | 10590.0 |
| | S4 | 10659.8 | 10660.0 |
| L-sTd | S1 | 10946.3 | 10945.9 |
| | S2 | 10642.8 | 10643.4 |
| | S3 | 10590.7 | 10590.7 |
| | S4 | 10659.8 | 10660.0 |
| M-sTd | S1 | 11869.0 | 11872.0 |
| | S2 | 11509.3 | 11510.0 |
| | S3 | 11513.4 | 11513.8 |
| | S4 | 11540.4 | 11541.0 |
| F-sTd | S1 | 11461.0 | 11460.5 |
| | S2 | 11101.3 | 11099.5 |
| | S3 | 11105.4 | 11104.7 |
| | S4 | 11132.4 | 11130.4 |

Figure 3:
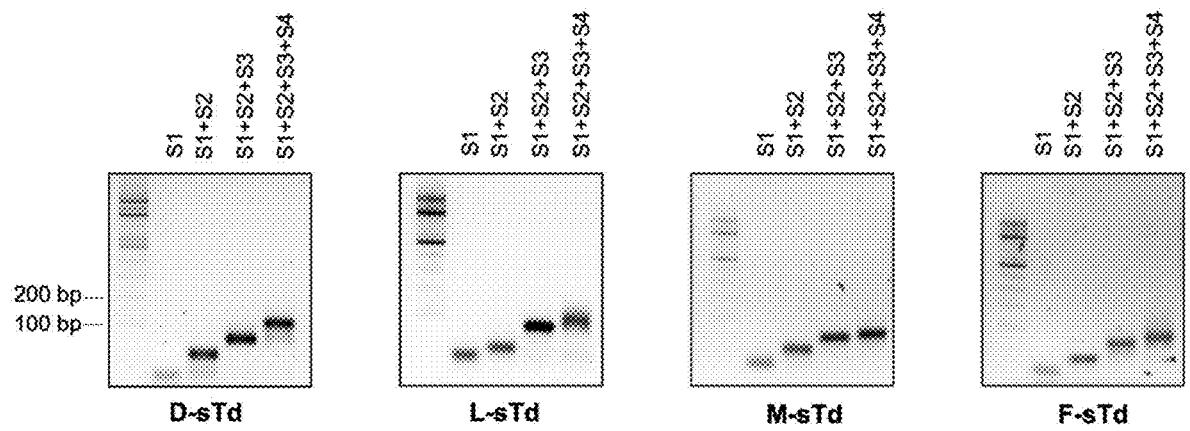
FIG. 3. Agarose gel (2%) electrophoresis of sTds (300 nM).

The self-assembly of the small tetrahedrons constructed using four oligonucleotides (S1-S4, Table 1) of each backbone was verified by agarose gel (2%) electrophoresis, which illustrated gradually retarded mobility of the constructs as the number of oligonucleotide strands increased (FIG. 3).

Example 2. Preparation of Self-Assembled sTds and Melting Temperature

The solution containing four oligonucleotides (S1-S4, 300 nM, Table 1) in TM buffer (5 mM $MgCl_2$, 10 mM Tris-HCl, pH 8.3) was heated to 95° C. for 10 min and slowly cooled to 4° C. for 24 h. The self-assembled structure was verified on agarose gel (2%) run for 40 min at 100 V in 0.5×TAE buffer. The nucleic acid bands in gel were stained by SYBR gold and imaged using the iBright FL1000 imaging system (Invitrogen, USA).

Fluorescence intensity of the mixture containing D-sTd (300 nM) and SYBR green (1×) in TM buffer was measured at varying temperature from 4° C. to 95° C. by using a real-time PCR machine (StepOne, Applied Biosystems, USA). Melting temperature was determined as the temperature at which (−dF/dT) was the highest. F and T denote fluorescence intensity and temperature, respectively.

As a result, the melting temperature of the tetrahedron with 10 bp per side as the core structure was much higher than 37° C. (FIG. 1).

Example 3. Assay of Properties of Nanostructures 3-1. Measurement of Hydrodynamic Size of TDN The hydrodynamic sizes and zeta-potential of tetrahedrons (1 TM buffer) were measured at room temperature using a Zetasizer (Malvern, UK).

As a result, the hydrodynamic size of sTds was approximately 6 nm, as measured by dynamic light scattering (DLS) (FIG. 2c).

3-2. Atomic Force Microscopy

The structural features of sTds including triangular vertices were also evidenced by the nanoscale images analyzed using atomic force microscopy (AFM). Specifically, the sTds assembled at 50 nM to 100 nM were diluted to 20 nM in TAE-Mg buffer (50 m Tris-acetate, 2 mM EDTA, 12.5 mM $MgCl_2$) and mixed with an equivalent volume of TAE-Mg including 10 mM $NiCl_2$. These solutions were placed onto mica pre-treated with TAE-Mg including 5 mM $NiCl_2$, and incubated at room temperature for 1 min. The samples were imaged in the non-contact mode on an AFM instrument (SCANASYST Multimode, Bruker, USA) using SCANASYST-FLUID+tips (Bruker, USA) in fluid.

As a result, the structural features of sTds including triangular vertices were also evidenced by the nanoscale images analyzed using AFM (FIG. 2b).

Example 4. Assay of Serum Stability of TDN

The sTds (2000 nM) were incubated in 50% mouse serum (25 μL) at 37° C. for 0 h, 1 h, 2 h, 3 h, 4 h, 5 h, 6 h, and 24 h. The reaction was quenched by 0.5 mM EDTA (2.5 μL). Then, the samples were treated with proteinase K (0.8 mg/mL, Bioneer, Korea) for 1 h in 5% SDS (50 μL). The mixture (100 μL) was with gel loading buffer (100 μL, 98% formamide, 0.5 M EDTA) and heated at 95° C. for 10 min. The mixture was analyzed on SYBR gold-containing agarose gel (1%). Gel images were obtained using the iBright FL1000 imaging system (Invitrogen, USA).

For pull-down assay of serum proteins bound to sTds, streptavidin-coated magnetic beads (30 μL, Dynabeads™ MyOne Streptavidin™ T1, Invitrogen, USA) were washed three times in buffer A (60 μL, 0.5 mM EDTA, 1 M NaCl, 5 mM Tris-HCl, pH 7.5). After the final wash, the washed beads were resuspended with 50% mouse serum (30 Sigma-Aldrich, USA) and binding buffer (30 μL, 1 mM EDTA, 2 M NaCl, 10 mM Tris-HCl, pH 7.5) at 37° C. for 1 h. The proteins non-specifically bound to the magnetic beads were removed. The protein supernatant (60 μL) was added to biotinylated sTds (2 μM) immobilized on streptavidin-coated magnetic beads, and the mixture was incubated at 37° C. for 1 h. Magnetic beads were separated from unbound serum proteins and washed with buffer A three times. Magnetic beads were resuspended in loading buffer (50 mM Tris-HCl, pH 6.8, 2% SDS, 6% (v/v) glycerol, 2 mM DTT, 0.01% (w/v) Bromophenol Blue) and incubated at 95° C. for 10 min. Proteins bound on sTds-immobilized magnetic beads were analyzed on 5% to 12% SDS-PAGE and silver-stained by EzStain Silver reagent (Atta, Japan) according to the manufacturer's instructions. Gel images were obtained using the iBright FL1000 imaging system (Invitrogen, USA).

As a result, when serum stability of sTds was estimated in 50% mouse serum, all of the unnatural backbone-based sTds (L-sTd, M-sTd, F-sTd) showed greatly improved serum stability compared with natural D-sTd, which was significantly degraded after incubation for 2 h in the serum solution (FIG. 2d).

Example 5. Confirmation of TDN Distribution In Vivo

The in vivo biodistribution of the nanostructures was examined. Healthy BALB/c nude mice were intravenously administered Cy5.5-labeled sTds and imaged using the IVIS system. Specifically, the animal study was approved by the animal care and use committee of the Korea Institute of Science and Technology, and all mice were handled in accordance with institutional regulations (2018-082). Male BALB/c nude mice (22 g to 24 g, 6 weeks old) were purchased from Orient Bio (Seoungnam, Korea). The mice were randomly divided into four groups (n=3 per group), and Cy5.5-sTds (2 μM, 200 μL) was intravenously administered to each. In vivo fluorescence was monitored for 24 h by an animal imaging system (IVIS, Caliper Science, USA). After 24 h, mice were scarified for ex vivo imaging of main organs. The excitation and the emission wavelengths were 660 nm and 710 nm, respectively. The obtained images were analyzed by the IVIS Living Imaging 3.0 software.

Figure 4:
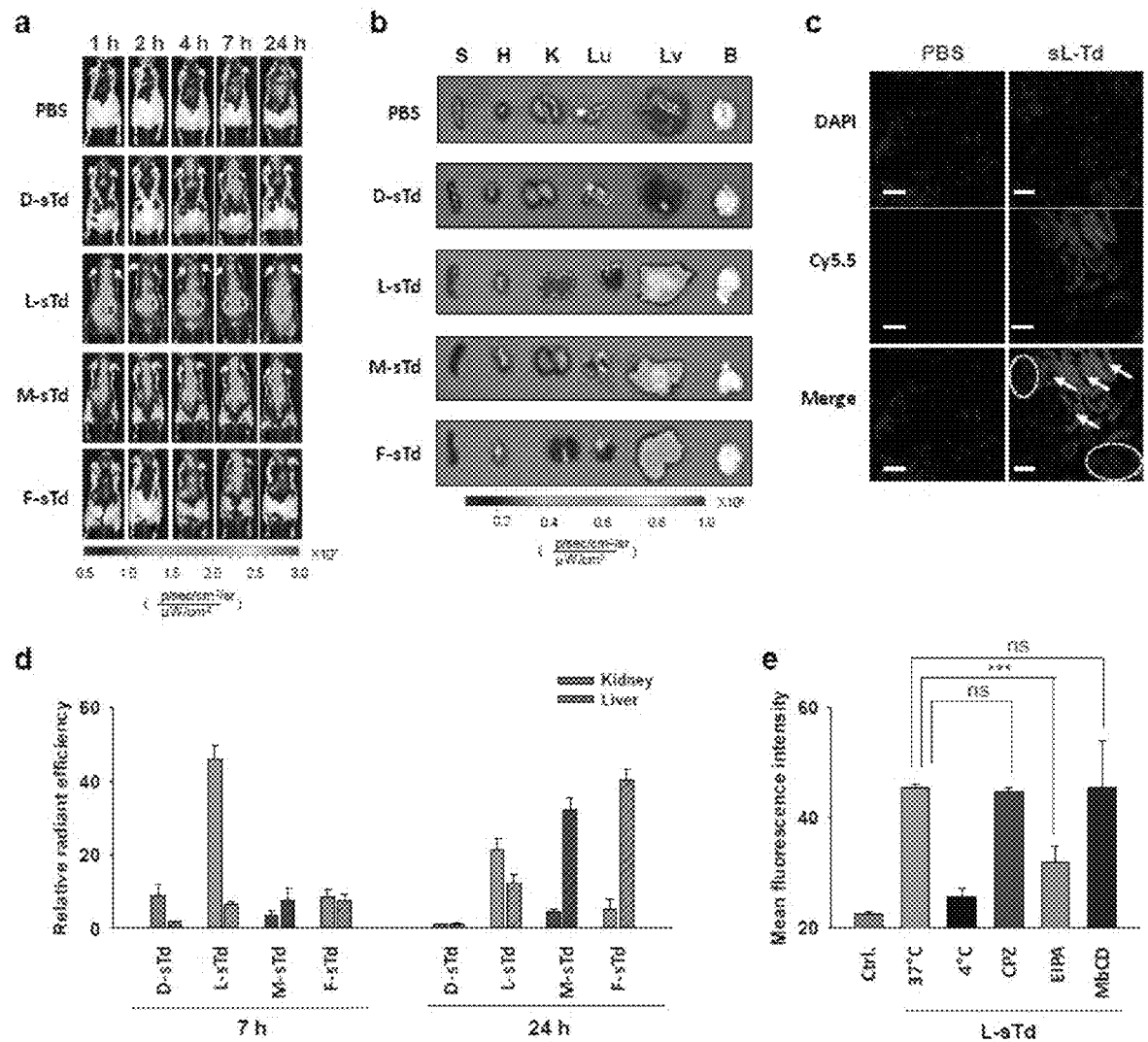
FIG. 4. In vivo behavior of sTds. (a) In vivo biodistribution of intravenously injected Cy5.5-sTds (2 µM, 200 µL) in healthy nude mice. (b) Ex vivo distribution of sTds imaged at 7 h post-injection. Scale bars indicate 40 µm. (c) Section images of kidney from mice injected with L-sTd (red) at 7 h post-injection. Nuclei were stained with DAPI (blue). Glomeruli and tubules are indicated with dotted circles and arrows, respectively. (d) Relative distribution levels of sTds in kidney or liver at 7 h and 24 h. (e) Cellular uptake efficiency of L-sTd in mouse kidney tubular epithelial cells (TCMK-1) in the presence of endocytosis inhibitors: chlorpromazine (CPZ, 10 µM, clathrin-mediated endocytosis), methyl-β-cyclodextrin (MbCD, 1 mM, caveolae-mediated endocytosis) or 5-(N-ethyl-N-isopropyl) amiloride (EIPA, 50 µM, macropinocytosis). The lowered uptake level at 4° C. indicated endocytosis of L-sTd. Data are represented as mean±standard deviation (SD) (n=3) with statistical significance (***$P<0.001$; ns, non-significant).

As a result, only L-sTd was substantially localized to the kidneys, whereas all of the other sTds did not show a considerable level of kidney distribution. The accumulation level of L-sTd in the kidneys was maximized at 7 h post-injection and decreased slowly over the next 17 h (FIG. 4a). Ex vivo images of the major organs harvested 7 h after the injection also displayed significantly high kidney distribution level of L-sTd (FIG. 4b). The accumulation level of L-sTd in the kidneys estimated by fluorescence intensity was 5 times higher than that in the liver, indicating that L-sTd is a kidney-specific nucleic acid nanostructure (FIGS. 4b and 4d).

Example 6. Histological Analysis of Kidney Tissue Section

Kidney tissues harvested from mice were fixed in 4% formaldehyde, paraffin-embedded, cut in 4 μm sections, stained with hematoxylin and eosin (H&E), and analyzed by optical microscopy (Eclipse Ti-S, Nikon, Japan). For fluorescent histological inspection, sections were deparaffinized in xylene, re-hydrated with serial treatment of ethanolic solutions (100%, 95%, 75%, and 50%), and washed with washing buffer (1×TBST, 0.05% Tween 20, 0.03% Triton X). Antigen retrieval was conducted by treating the sections with citrate buffer (10 mM sodium citrate, 0.05% Tween, pH 6.0) for 20 min. Then, the sections were treated with M.O.M. blocking buffer (Vector Laboratories, USA) for 1 h and 5% BSA/PBST for 5 min. Monoclonal anti-p53 was added to the sections and incubated at 4° C. overnight in a humid chamber. After washing with a washing buffer, the sections were treated with rabbit anti-mouse IgG secondary antibody conjugated with AlexaFluor 488 (1:2000, ThermoFisher Scientific, USA) for 2 h. The sections were rinsed, dried, and then mounted with DAPI solution (Abcam, UK). Finally, the sections were imaged by fluorescence microscopy (Axio Observer 3, Carl Zeiss, Germany).

In the histological analysis of the kidney, the fluorescence of L-sTd was observed in tubules (FIG. 4c), suggesting that the nanostructure could successfully penetrate into kidney tissue after glomerular filtration. D-sTd showed a low kidney accumulation level, possibly due to degradation to small fragments subject to renal clearance. Other serum-stable unnatural backbone-based tetrahedrons such as M-sTd and F-sTd also showed a low kidney accumulation level.

Example 7. Cellular Uptake Mechanisms

The uptake mechanism of L-sTd was examined when it was internalized into tubular cells (TCMK-1). TCMK-1 (mouse tubular epithelial cell line) cells were obtained from the Korean cell line bank (Korea). Cells were cultured in RPMI medium supplemented with 10% fetal bovine serum and 1% penicillin-streptomycin. Cells with 80% to 90% confluency were used for experiments. Cells ($1 \times 10^5$ cells) pre-incubated with inhibitors chlorpromazine (CPZ, 10 μM), methyl-β-cyclodextrin (MβCD, 1 mM), or ethylisopropylamiloride (EIPA, 50 μM) for 30 min were treated with FAM-labeled sTds (200 nM) in serum-free RPMI at 37° C. in a 5% $CO_2$ incubator. After 6 h, cells were harvested and washed twice with cold PBS (1 mL). Cellular uptake of sTds was estimated by quantifying fluorescent cells by flow cytometry (Guava, Millopore, USA).

As a result, uptake of L-sTd was decreased in the presence of 5-(N-ethyl-N-isopropyl)amiloride (EIPA), an inhibitor of macropinocytosis, indicating that L-sTd was endocytosed into tubular cells by macropinocytosis (FIG. 4e).

Having investigated the possible mechanisms that drive L-sTd into the kidneys, an attempt was made to use L-sTd as a carrier for the kidney-targeted delivery of siRNA to treat AKI.

Example 8. siP53@L-sTd Preparation and p53 Knockdown

Figure 5:
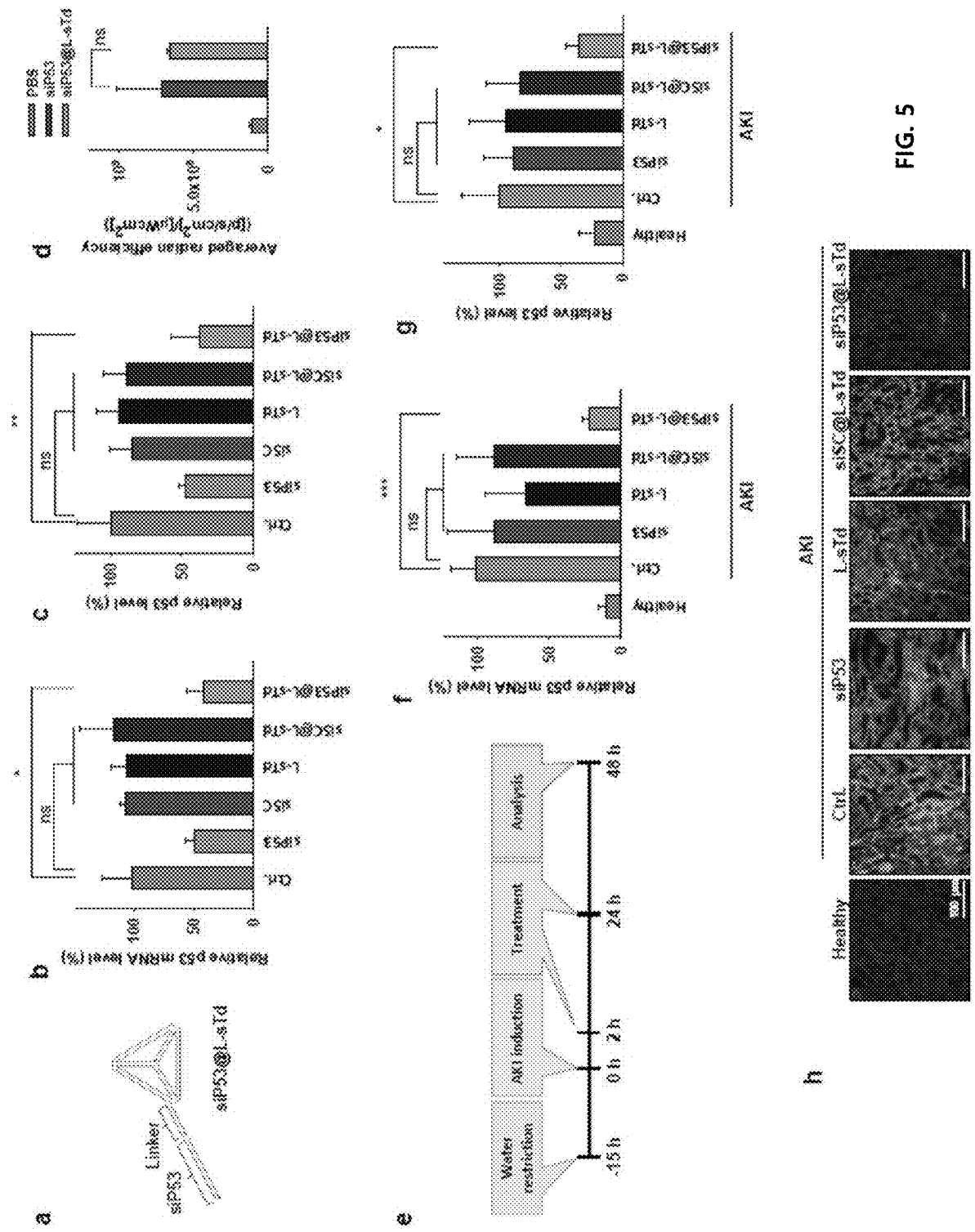
FIG. 5. Potency of siP53 delivered by L-sTd. (a) Schematic structure of siP53 loaded in L-sTd (siP53@L-sTd). In vitro potency of siP53 estimated by (b) qRT-PCR analysis of p53 mRNA level and (c) western blotting of p53 in TCMK-1 cells (mean±SD, n=3; $P<0.01$; ns, non-significant). (d) Kidney distribution level of siP53 and siP53@L-sTd (mean±SD, n=3; ns, non-significant). (e) Preparation of AKI mice and treatment schedule to analyze in vivo potency of siP53. In vivo potency of siP53 (0.25 mg/kg per injection) in AKI mice was estimated by (f) qRT-PCR analysis of p53 mRNA level and (g) western blotting of p53 in kidney tissue lysate (mean±SD, n=5; *$P<0.001$; *$P<0.05$; ns, non-significant). GAPDH was used as the internal control to determine relative p53 mRNA levels. β-Actin was used as the internal control to determine relative p53 protein levels. (h) Immunofluorescence analysis of p53 expression (green) on kidney sections. Nuclei were stained with DAPI (blue). Scale bars indicate 100 µm.

L-sTd loaded with siRNA targeting p53 mRNA (siP53@L-sTd) was prepared by hybridization of 10-mer 2'-O-Me-RNA linker with 10-mer D-DNA 3'-overhang of the sense strand of siP53 (FIG. 5a, Table 1, and FIG. 6). Specifically, in order to prepare siP53@L-sTd, a single-stranded L-Td having an overhang arm (10-mer) was designed. The 5' end of the sense sequence of siP53 was also extended to 10-mer, and si-p53 was assembled into L-sTd through complementary base pairs (FIG. 6).

To ensure in vivo stability of siRNA, 2'-O-Me-modified siP53 was employed. Since L-DNA is unable to hybridize with D-DNA, 2'-O-Me-RNA, which can form a duplex with D-DNA and has similar serum stability to L-DNA, was used as the linker. The mobility of siP53@L-sTd was slightly lower than L-sTd in agarose gel (FIG. 7).

The gene silencing effect of siP53@L-sTd was initially examined in TCMK-1 cells. After treatment of the cells with siP53@L-sTd, the target mRNA level was analyzed using quantitative reverse-transcriptase PCR (qRT-PCR) and the lowered mRNA level downregulated p53 protein expression, as observed by western blotting analysis.

For PCR (qRT-PCR), TCMK-1 cells seeded onto a 12-well plate ($2 \times 10^5$ cells/well) were treated with siP53@L-sTd (200 nM) in serum-free RPMI at 37° C. in a 5% $CO_2$ incubator. After 48 h, total RNA was extracted from the cells using a RNeasy Minikit (Quiagen, UK). The reverse transcription was conducted with isolated RNA (2 μg) to prepare cDNA using a Reverse Transcription Kit (Enzynomics, Inc.). PCR of p53 cDNA (target gene) and GAPDH cDNA (control gene) was performed using Power SYBR®-Green PCR master mix (Invitrogen, USA). The quantitative amplification curve of PCR was monitored by StepOne Real-Time PCR system (Applied Biosystems). The relative p53 mRNA level was obtained by normalization of p53 to GAPDH mRNA level. For estimation of p53 mRNA level in vivo, total RNA was extracted from homogenized kidney tissues and amplified in the same manner. Primer sequences used for qRT-PCR are shown in Table 3.

TABLE 3

| Primer | Sequence |
| --- | --- |
| Mouse p53-F | ACAGCGTGGTGGTACCTTAT (SEQ ID NO: 10) |
| Mouse p53-R | TATACTCAGAGCCGGCCT (SEQ ID NO: 11) |
| Mouse GADPH-F | TGCACCACCAACTGCTTAG (SEQ ID NO: 12) |
| Mouse GADPH-R | GGATGCAGGGATGATGTTC (SEQ ID NO: 13) |

As a result, as shown in FIG. 5b, the mRNA level of the cells treated with siP53@L-sTd was 40% lower than the gene level of the untreated control cells. The gene-silencing effect of siP53@L-sTd was similar to that of siP53 delivered using the conventional transfection agent, lipofectamine, indicating that the target gene can be efficiently downregulated by treatment with siP53@L-sTd. When siRNA with a scrambled sequence was delivered by L-sTd (siSC@L-sTd), no significant change in the gene level was observed, showing that the gene-silencing by siP53@L-sTd is a target-specific event.

For western blotting analysis, TCMK-1 cells or homogenized kidney tissues were lysed in RIPA containing protease inhibitors at 4° C. overnight. The mixture was centrifuged at 12,000 rpm for 20 min at 4° C. Proteins (20 μg) in the supernatant were separated by 5% to 12% SDS-PAGE and transferred to PVDF membrane (100 min, 350 mA). After blocking with 5% BSA (w/v) in TBST buffer for 1 h at room temperature, the membrane was incubated with solutions containing monoclonal anti-p53 (1:1000), anti-caspase-3 (1:1000), anti-GADPH (1:1,000), and β-actin (1:1000) (Cell Signaling Technology, USA) at 4° C. overnight. Then, they were incubated with a horseradish peroxidase (HRP)-conjugated secondary antibody (1:3,000) at room temperature for 1 h. After washing, the protein bands were visualized using Super Signal™ West Pico Chemiluminescent (Thermo Fisher Scientific, USA) and imaged using the iBright FL1000 imaging system (Invitrogen, USA).

As a result, the lowered mRNA level downregulated p53 protein expression, as observed by western blotting analysis (FIGS. 5c and 8).

Example 9. Preparation of AKI Mouse Model and Treatment with Td-p53

It was examined whether the p53 gene silencing can be achieved to suppress the development of AKI in the AKI animal model established with BALB/c mice. Specifically, the AKI animal model was established by single intraperitoneal injection (intraperitoneal administration) of the folic acid solution (350 μL, 250 mg/mL in 100 mM $NaHCO_3$, pH 8.8) into BALB/c mice by following a previously reported procedure (Gupta A, Puri V, Sharma R, Puri S, Exp Toxicol Pathol., 2012, 64 (3), 225-32.). AKI mice were divided randomly in 5 groups (n=5 per group). At 2 h and 24 h after treatment of folic acid, each group of AKI mice was intravenously administered with PBS (200 μL), siP53 (2 μM, 200 μL), L-sTd (2 μM, 200 μL), siSC@L-sTd (2 μM, 200 μL), or siP53@L-sTd (2 μM, 200 μL). The siRNA dose in each group was approximately 0.25 mg/kg per injection (FIG. 3e). After another 24 h, all mice were scarified, and the kidneys were harvested for further ex vivo analysis of the therapeutic effect of siRNA.

As a result, the kidney-specific delivery of siRNA was successfully performed by L-sTd (FIGS. 5d and 9). Similarly, naked siRNA (siP53) was also accumulated in the kidneys due to its concise structure and serum stability.

The qRT-PCR analysis revealed that the p53 mRNA level in kidney tissue of AKI mice was 9 times higher than that in healthy mice (FIG. 5f). The upregulated gene level in kidney tissue of AKI mice was decreased by 70% after treatment with siP53@L-sTd. The gene-silencing effect by siP53, vehicle alone (L-sTd), or siSC@L-sTd was not significant, demonstrating that only the siRNA with a target-specific sequence delivered by L-sTd could downregulate the target gene in a sequence-specific manner. Consistently, decrease in p53 protein expression was substantially observed by western blotting analysis only in the group treated with siP53@L-sTd (FIGS. 5g and 10). Downregulated p53 expression level by treatment with siP53@L-sTd was also revealed by immunofluorescence analysis of the kidney tissue section (FIG. 5h). In addition, the expression of caspase-3, a downstream factor in p53-driven apoptosis signal cascade, was also lowered by 70% after treatment with siP53@L-sTd, as analyzed by western blotting, whereas no significant decrease in caspase-3 level was observed in the other groups treated with siP53, L-sTd, and siSC@LsTd (FIG. 11).

Although naked siP53 was able to reach the kidney, it failed to downregulate the target gene. This was due to low cellular uptake efficiency and unsuccessful endosomal escape of naked siP53. Flow cytometric analysis of TCMK-1 cells treated with fluorescein-labeled siP53 reveals substantially lower uptake level of siP53 than that of siP53@L-sTd (FIG. 12a).

As fluorescein is a pH-sensitive dye showing greatly reduced intensity at endosomal pH, endosomal entrapment can also be indicated by the increase of fluorescence intensity of cells after treatment with chloroquine (CQ), which can facilitate endosomal escape. Specifically, for endosomal escape analysis, TCMK-1 cells ($1 \times 10^5$ cells) pre-treated with CQ (100 μM) were incubated with fluorescein-labeled siP53 or siP53@L-sTd (200 nM) in serum-free RPMI for 6 h. The uptake level was analyzed by flow cytometry and compared with that without CQ pre-incubation.

As shown by the results, CQ treatment significantly increased the relative mean fluorescence intensity of siP53-treated cells (FIG. 12b). This shows that the major portion of siP53 internalized in the cells was entrapped in endosomes, and thereby failed to show an activity on the target gene in cytoplasm. By contrast, CQ treatment did not affect the fluorescence intensity of siP53@L-sTd-treated cells (FIG. 12b), suggesting that siP53@L-sTd could escape endosomes, thereby successfully downregulating the target gene in cytoplasm. Sufficient cytosolic delivery of siP53 by L-sTd led to the considerable silencing effect of the siRNA even at a dose 20 times lower than that used in a previous study (Molitoris, B. A. et al. siRNA targeted to p53 attenuates ischemic and cisplatin-induced acute kidney injury. Journal of the American Society of Nephrology 2009, 20 (8), 1754-1764.).

Example 10. Effect of Inducing Apoptotic Damages

To examine whether the lowered p53 level by siP53@L-sTd could alleviate apoptotic damage induced in AKI, the kidney section was visualized after labeling the damaged region with fluorescent annexin V. Specifically, kidney was excised from mice intravenously injected with Cy5.5-labeled L-sTd at 7 h post-injection. A freshly dissected kidney tissue was embedded in optimum cutting temperature (OCT) compound (Leica Biosystems, Germany) and frozen completely at −80° C. The frozen tissue block was sectioned with 4 μm thickness by a cryotome (Labcore Inc, Korea).

To analyze apoptotic damage in the sections, the deparaffinized sections were treated with Cy5-labeled annexin V (Abcam, UK) and imaged using fluorescence microscopy (Axio Observer 3, Carl Zeiss, Germany).

Compared with the healthy mice, AKI mice illustrated a wide region of damaged cells in the kidney section. The damage was significantly alleviated in the siP53@L-sTd-treated group, showing that siRNA treatment could considerably prevent apoptotic damage in AKI. This is consistent with the data observed in western blotting and qRT-PCR of p53. However, siP53, L-sTd, and siSC@L-sTd did not show any potency against the apoptotic damage in kidney tissue.

The extent of damage recovery in the cortex and medulla of kidney tissue sections mounted with DAPI solution (Abcam, UK) (FIG. 13a) or stained with hematoxylin and eosin (H&E) (FIG. 13b) was also examined. The integrity of the renal structure in AKI mice was severely damaged resulting in significantly widened Bowman's space of glomeruli (red arrows) in the cortex and dilation (yellow arrows) of tubules in the cortex and medulla. Only treatment with siP53@L-sTd could restore the morphology of renal tubules and glomeruli significantly. The enlarged sizes of glomeruli (10% to 20%) and tubules (30% to 40%) in the AKI model were shrunken to sizes close to the healthy size only after treatment with siP53@L-sTd, while other treatments were not effective in restoring the sizes (FIG. 13c).

Example 11. Serum Analysis

BUN and serum CRE levels were measured in mice which are typical diagnostic indicators for AKI. Specifically, blood samples were collected from mice (n=4 per group) at 48 h after AKI induction, clotted at room temperature for 30 min, and centrifuged at 2,000 g at 4° C. for 15 min. The amounts of creatine and BUN in the supernatant were analyzed by SCL Healthy Inc. (Korea).

As a result, the creatinine and BUN levels in AKI mice were significantly decreased only after treatment with siP53@L-sTd (FIG. 13d), which clearly confirms that the p53 siRNA delivered into the kidneys using L-sTd is effective for the recovery of kidney function.

From the above description, those skilled in the art to which the present invention pertains will be able to understand that the present invention can be embodied into different and more detailed modes, without departing from the technical spirit or essential features thereof. In this regard, it will be understood that the embodiments described above are only illustrative, and should not be construed as limiting. The scope of the present invention should be construed such that all changes or modifications derived from the meaning and scope of the claims to be described below and equivalent concepts thereof, rather than the above detailed description, are included in the scope of the present invention.

The invention claimed is:

1. A kidney-specific drug delivery system comprising three-dimensional self-assembled nucleic acid nanoparticles having a tetrahedral structure, wherein the nucleic acid nanoparticles consist of one or more oligonucleotides selected from the group consisting of SEQ ID Nos: 1 to 4.

2. The kidney-specific drug delivery system of claim 1, wherein the oligonucleotide consists of any one selected from the group consisting of D-DNA, L-DNA, 2'-fluoro-RNA, and 2'-O-methoxy-RNA.

3. The kidney-specific drug delivery system of claim 1, wherein the oligonucleotide consisting of the nucleotide sequence of SEQ ID NOs: 1 to 4 consists of any one of 2'-fluoro-RNA and 2'-O-methoxy-RNA.

4. The kidney-specific drug delivery system of claim 1, wherein a number of the oligonucleotides forming the nucleic acid nanoparticles is four.

5. The kidney-specific drug delivery system of claim 1, wherein the nucleic acid nanoparticles comprise a double-stranded nucleic acid including a hybridization region in which the oligonucleotide and the oligonucleotide hybridizing thereto are hybridized, wherein the double-stranded nucleic acid forms a side of a surface of a nucleic acid nanoparticle structure.

6. The kidney-specific drug delivery system of claim 1, wherein the drug delivery system further comprises a pharmaceutically active ingredient.

7. A pharmaceutical composition, comprising:
a kidney-specific drug delivery system of claim 1; and
a pharmaceutically active ingredient bound to the drug delivery system.

8. The pharmaceutical composition of claim 7, wherein the pharmaceutical composition comprises:
a first oligonucleotide including D-DNA or L-DNA bound to the 3' end of any one of four oligonucleotides forming the three-dimensional self-assembled nucleic acid nanoparticles of the drug delivery system;
a second oligonucleotide hybridized to the first oligonucleotide to form a duplex; and
a pharmaceutically active ingredient linked to the second oligonucleotide forming the duplex.

9. The pharmaceutical composition of claim 7, wherein the pharmaceutically active ingredient inhibits a gene upregulating an apoptosis pathway.

10. The pharmaceutical composition of claim 9, wherein the gene upregulating an apoptosis pathway is any one or more selected from the group consisting of p53, Fas, a tumor necrosis factor-related apoptosis-inducing ligand (TRAIL), a tumor necrosis factor (TNF), receptors thereof, bcl-2 and caspase.

11. The pharmaceutical composition of claim 10, wherein the gene is p53.

12. The pharmaceutical composition of claim 7, wherein the pharmaceutically active ingredient is any one or more selected from the group consisting of siRNA, shRNA, an antisense oligonucleotide, and microRNA.

* * * * *